United States Patent
Tang et al.

(10) Patent No.: US 10,532,012 B2
(45) Date of Patent: Jan. 14, 2020

(54) CORE SHELL SILICA AND METHODS FOR THE SAME

(71) Applicant: Colgate-Palmolive Company, New York, NY (US)

(72) Inventors: Saide Tang, Kendall Park, NJ (US); Lin Fei, Kendall Park, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 59 days.

(21) Appl. No.: 15/680,391

(22) Filed: Aug. 18, 2017

(65) Prior Publication Data

US 2019/0053992 A1 Feb. 21, 2019

(51) Int. Cl.
| | | |
|---|---|---|
| *A61K 8/25* | (2006.01) | |
| *A61K 8/34* | (2006.01) | |
| *A61Q 11/00* | (2006.01) | |
| *A61K 8/19* | (2006.01) | |
| *A61K 8/27* | (2006.01) | |
| *A61K 8/11* | (2006.01) | |
| *B01J 13/02* | (2006.01) | |
| *B01J 13/22* | (2006.01) | |
| *B01J 13/20* | (2006.01) | |

(52) U.S. Cl.
CPC ............... *A61K 8/25* (2013.01); *A61K 8/11* (2013.01); *A61K 8/19* (2013.01); *A61K 8/27* (2013.01); *A61K 8/345* (2013.01); *A61Q 11/00* (2013.01); *B01J 13/02* (2013.01); *B01J 13/20* (2013.01); *B01J 13/22* (2013.01); *A61K 2800/621* (2013.01); *A61K 2800/651* (2013.01)

(58) Field of Classification Search
CPC .................................. A61K 8/19; A61K 8/25
See application file for complete search history.

(56) References Cited

U.S. PATENT DOCUMENTS

| | | |
|---|---|---|
| 2016/0331653 A1 | 11/2016 | Maloney et al. |
| 2016/0338919 A1 | 11/2016 | Pan et al. |
| 2016/0338920 A1 | 11/2016 | Pan et al. |

FOREIGN PATENT DOCUMENTS

CN          1695447 A       11/2005

OTHER PUBLICATIONS

Chemical Land 21, 2018, "Zinc Nitrate Hexahydrate (Nitric Acid, Zinc Salt)," http://www.chemicalland21.com/industrialchem/inorganic/zinc_nitrate_hexahydrate.htm.
International Search Report and Written Opinion of the International Searching Authority in International Application No. PCT/US2017/047494, dated Jan. 24, 2018.

*Primary Examiner* — Kyle A Purdy

(57) ABSTRACT

Methods for preparing high loading core shell silica (CSS) particles, or CSS particles having a relatively greater amount of surface active silicate groups than CSS particles prepared according to conventional methods is provided. The method may include contacting silica particles with a base having a first metal ion to produce core shell silica particles. Each of the core shell silica particles may include a silica core and a silicate of the first metal ion etched on a surface of the silica core. The method may also include contacting each of the core shell silica particles having the silicate of the first metal ion with an acidic aqueous solution including a metal salt having a second metal ion to produce core shell silica particles including the silica core and a silicate of the second metal ion on the surface of the silica core.

13 Claims, 1 Drawing Sheet

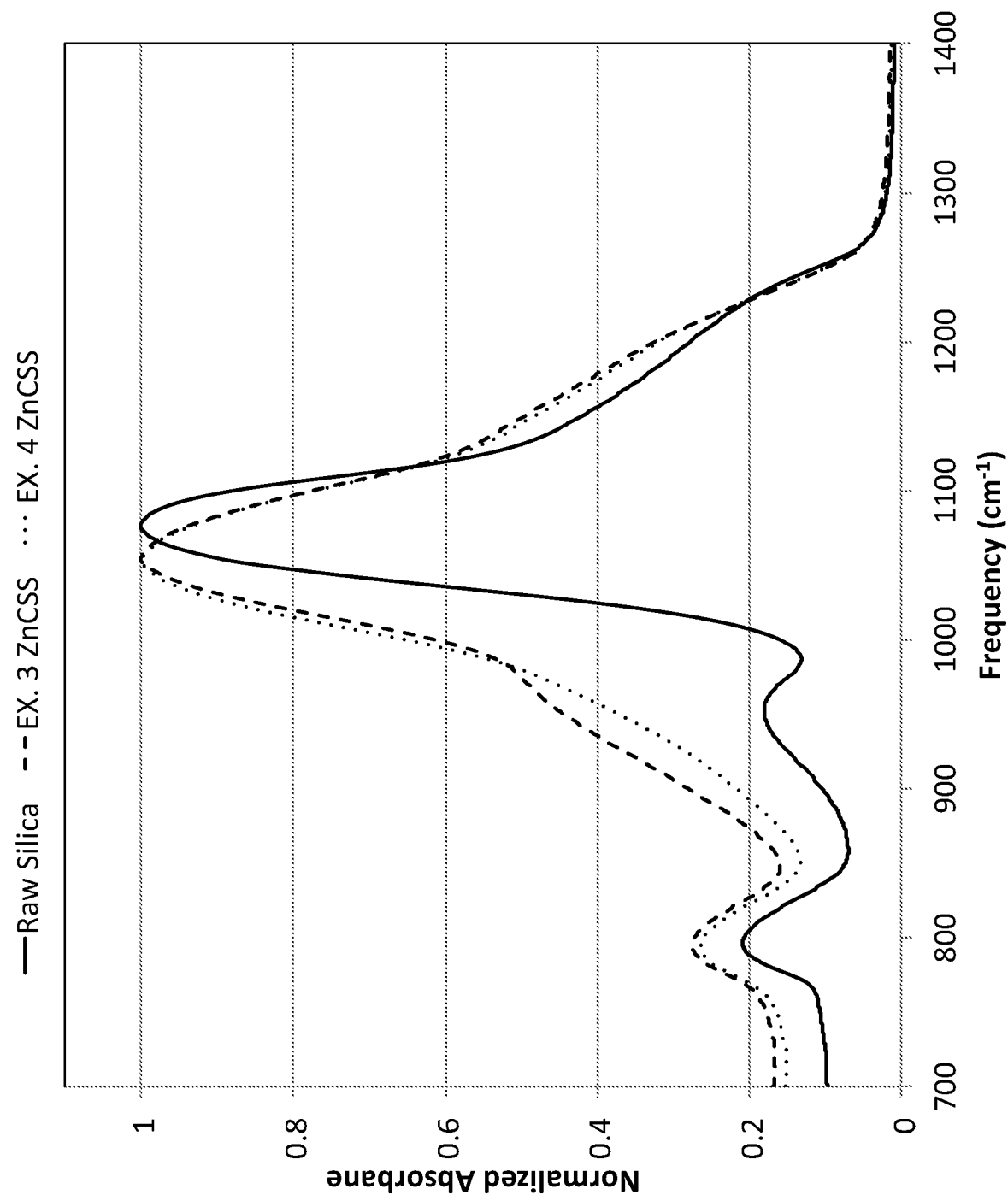

CORE SHELL SILICA AND METHODS FOR THE SAME

BACKGROUND

Conventional oral care compositions often include one or more active and/or benefit agents to provide the oral care composition with additional desired properties. For example, conventional oral care compositions may include an antibacterial agent and a tartar-control agent to provide an antibacterial and an anti-tartar effect, respectively. While the inclusion of the active and/or benefit agents are capable of providing desired properties to the oral care compositions, the increasing number of active and/or benefit agents included in the oral care compositions may raise regulatory concerns, increase the possibility of aversion from the consumer (e.g., sensitivity, allergy, taste, etc.), and increase the likelihood of incompatibility with other components of the oral care compositions.

In view of the foregoing, oral care compositions may often incorporate core shell particles to transport, carry, or otherwise deliver active and/or benefit agents to surfaces of an oral cavity. For example, oral care composition may often utilize core shell silica (CSS) particles to deliver one or more active and/or benefit agents to the surfaces of the oral cavity. Particularly, the CSS particles have an anionic surface capable of delivering various metal ions (e.g., $Zn^{2+}$, $Ca^{2+}$, etc.) as active and/or benefit agents to the surfaces of the oral cavity. Conventional CSS particles, however, exhibit relatively low capacity and/or loading of the metal ions, thereby limiting the amount of the active and/or benefit agents delivered to the oral cavity.

What is needed, then, are improved core shell silica particles for oral care compositions and methods for making the core shell silica particles.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a method for preparing high loading core shell silica (CSS) particles, or CSS particles having a relatively greater amount of surface active silicate groups than CSS particles prepared according to conventional methods. The method may include contacting silica particles with a base having a first metal ion to produce core shell silica particles. Each of the cores shell silica particles may include a silica core and a silicate of the first metal ion etched on a surface of the silica core. The method may also include contacting each of the core shell silica particles having the silicate of the first metal ion with an acidic aqueous solution including a metal salt having a second metal ion to produce core shell silica particles including the silica core and a silicate of the second metal ion on the surface of the silica core.

In at least one implementation, the first metal ion is a monovalent ion, optionally a group 1 metal ion.

In at least one implementation, the acidic aqueous solution further includes a humectant In at least one implementation, the humectant of the acidic aqueous solution is at least one of ethanol, polyhydric alcohol, such as glycerin, glycol, inositol, maltitol, mannitol, sorbitol, xylitol, propylene glycol, polypropylene glycol (PPG), and polyethylene glycol (PEG).

In at least one implementation, the humectant is sorbitol.

In at least one implementation, contacting each of the core shell silica particles with the acidic aqueous solution includes incrementally adding the core shell silica particles to the acidic aqueous solution.

In at least one implementation, the silica particles include at least one of precipitated silica, fumed silica, and fused silica.

In at least one implementation, the base includes at least one of sodium hydroxide, potassium hydroxide, sodium carbonate, potassium carbonate, trisodium phosphate, disodium phosphate, potassium phosphate, dipotassium phosphate, tetrasodium pyrophosphate, and tetrapotassium pyrophosphate.

In at least one implementation, the base includes potassium hydroxide or sodium hydroxide.

In at least one implementation, a weight ratio of the silica particles to the base is from about 0.1:1 to less than 4:1, 0.1:1 to less than 3:1, about 1.3:1 to about 1.5:1, or about 1.4:1.

In at least one implementation, the second metal ion is a divalent metal ion, a trivalent metal ion, or a tetravalent metal ion.

In at least one implementation, the metal salt is a zinc salt, and the second metal ion is $Zn^{2+}$.

In at least one implementation, a weight ratio of the humectant to the base is from about 4.5:1 to about 8.5:1, about 6.2:1 to about 6.8:1, about 6.3:1 to about 6.5:1, or about 6.4:1.

In at least one implementation, a weight ratio of the humectant to the metal salt is from about 10:1 to about 13:1, about 11.4:1 to about 11.6:1, or about 11.5:1.

In at least one implementation, the acidic aqueous solution has a pH of less than 7, about 3.5 to about 4.5, or about 4.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF THE DRAWINGS

The present disclosure is best understood from the following detailed description when read with the accompanying FIGURE. It is emphasized that, in accordance with the standard practice in the industry, various features are not drawn to scale. In fact, the dimensions of the various features may be arbitrarily increased or reduced for clarity of discussion.

FIG. 1 illustrates an FTIR spectrum of raw silica, and ZnCSS particles prepared according to Examples 3 and 4.

DETAILED DESCRIPTION

The following description of various aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered methods for making or preparing high loading core shell silica (CSS) particles, or CSS particles having a relatively greater amount of surface active silicate groups than CSS particles prepared according to conventional methods.

Methods

The present disclosure may provide methods for making or preparing core shell silica (CSS) particles having a relatively greater amount of surface active silicate groups than CSS particles prepared according to conventional methods. The method may include contacting silica (e.g., silica particles) and a base having a metal ion, such as a first metal ion, with one another to prepare CSS particles having a silica core and a surface etched with a silicate of the first metal ion, or first metal silicate. In at least one implementation, the silica may be admixed or otherwise dispersed in water, and the base, which may be provided as a solid or an aqueous solution, may be combined or otherwise contacted with the water to contact the silica with the base. In another implementation, the silica may be directly contacted with the base. For example, the silica may be contacted with an aqueous solution of the base. The method may also include reacting or otherwise contacting the CSS particles having their respective surfaces etched with the first metal silicate with a metal salt having a metal ion, such as a second metal ion, to provide the surface of the CSS particles with a silicate of the second metal ion, or second metal silicate. In a preferred implementation, the CSS particles having the first metal silicate may be contacted with an aqueous solution of the metal salt having the second metal ion. The aqueous solution of the metal salt having the second metal ion may have or be adjusted to have an acidic pH. The aqueous solution of the metal salt having the second metal ion may preferably include a humectant.

As discussed above, the method may include contacting the silica (e.g., silica particles) with the base having the first metal ion to prepare the CSS particles having the silica core, where the surface of the silica core is etched with the silicate of the first metal ion, or the first metal silicate. As used herein, the term "etched," "etched silica," or "etched silica core," may refer to a silica core having a surface at least partially dissolved, where a metal silicate (e.g., the first metal silicate) is formed on, along, or about the silica core. It should be appreciated that the first metal silicates dispersed along the surface of the silica core are not additional layers coated on top of the original surface of the silica. For example, contacting the silica with the base may reduce respective diameters of the silica, thereby providing the silica core having the first metal silicate along the surface thereof. The first metal silicate formed along the surface of the silica core may be represented by formula (1),

$$M^1_2SiO_3 \cdot xH_2O \qquad (1)$$

where $M^1$ is a monovalent metal ion, such as an alkali metal ion, and x is an integer from 0 to 10.

The base may be in the form of a solid or an aqueous solution. The base may have or include a first metal ion. The base may have a pKb of from about 0.1 to about 3. The first metal ion of the base may be a monovalent metal ion. In at least one implementation, the first metal ion of the base may be a group 1 or alkali metal ion. For example, the first metal ion of the base may be or include a sodium ion or a potassium ion. Illustrative bases may include, but are not limited to, sodium hydroxide, potassium hydroxide, sodium carbonate, potassium carbonate, trisodium phosphate, disodium phosphate, potassium phosphate, dipotassium phosphate, tetrasodium pyrophosphate, tetrapotassium pyrophosphate, and the like, and combinations thereof. In a preferred implementation, the base may be or include sodium hydroxide and/or potassium hydroxide. For example, the base may be a 50% aqueous solution of sodium hydroxide and/or a 45% aqueous solution of potassium hydroxide.

The silica may be or include any suitable silica capable of or configured to react with the base to form the CSS particles having the first metal silicate along the surface thereof. The silica may be in the form of particulates (e.g., silica particles), colloids (e.g., colloidal silica), amorphous silica, silica gel, and the like, and combinations thereof. Illustrative silica may be or include, but are not limited to, precipitated silica, fumed silica, fused silica, and the like, and combinations thereof. For example, the silica may be or include, but is not limited to, any one or more of ZEODENT® 114, ZEODENT® 105, ZEODENT® 165, and the like, which are commercially available from Huber Engineered Materials of Atlanta, Ga., SILODENT® Silicas and SYLOID® Silicas, which are commercially available from W.R. Grace of Houston, Tex., SORBISIL® Silicas, which are commercially available from PQ Corp. of Malvern, Pa., AEROSIL®, which is commercially available from Evonik Corp. of Parsippany, N.J., CAB-O-SIL®, which is commercially available from Cabot Corp. of Alpharetta, Ga., TECO-SIL®, which is commercially available from C-E Minerals, Inc. of Roswell, Ga., SPHERON®, which is commercially available from Japanese Glass Co., TIXOSIL® Silicas, which are commercially available from Solvay of Houston, Tex., and the like, and combinations thereof. Illustrative silica may also be or include, but are not limited to, sodium silicates, which are discussed and described in U.S. application Ser. No. 15/106,426, filed Dec. 18, 2014, and published as U.S. Pub. No. 2016/0338919, the contents of which are incorporated herein by reference to the extent consistent with the present disclosure. The silica may also be or include, but are not limited to, silica abrasives, such as silica gels and precipitated amorphous silica.

The silica may have an average particle size of from about 3 μm to about 12 μm. For example, the silica, which may be colloidal particles/particulates, may have an average particle size of from about 3 μm, about 4 μm, about 5 μm, about 6 μm, or about 7 μm to about 8 μm, about 9 μm, about 10 μm, about 11 μm, or about 12 μm. In another example, the silica may have an average particle size of from about 3 μm to about 12 μm, about 4 μm to about 11 μm, about 5 μm to about 10 μm, about 6 μm to about 9 μm, or about 7 μm to about 8 μm.

A weight ratio of the amount of the silica to the amount of the base may vary widely. In at least one implementation, the weight ratio of the silica to the base may be from greater than or equal to 0.1:1 to less than 4:1. For example, the weight ratio of the silica to the base may be from about 0.1:1, about 0.5:1, about 1.0:1, about 1.5:1, about 1.6:1, about 1.7:1, about 1.8:1, or about 1.9:1 to about 2.1:1, about 2.2:1, about 2.3:1, about 2.4:1, about 2.5:1, about 3.0:1, about 3.5:1, or less than 4.0:1. In another example, the weight ratio of the silica to the base may be from about 0.1:1 to about 4.0:1, about 0.5:1 to about 3.5:1, about 1.0:1 to about 3.0:1, about 1.5:1 to about 2.5:1, about 1.6:1 to about 2.4:1, about 1.7:1 to about 2.3:1, about 1.8:1 to about 2.2:1, or about 1.9:1 to about 2.1:1. In another implementation, the weight ratio of the silica to the base may be from greater than or equal to 0.1:1 to less than 3:1. For example, the weight ratio of the silica to the base may be from about 0.1:1, about 0.5:1, about 1.0:1, about 1.1:1, about 1.2:1, about 1.3:1, or about 1.4:1 to about 1.6:1, about 1.7:1, about 1.8:1, about 1.9:1, about 2.0:1, about 2.5:1, or about 3.0:1. In another example, the weight ratio of the silica to the base may be from about 0.1:1 to about 3.0:1, about 0.5:1 to about 2.5:1, about 1.0:1 to about 2.0:1, about 1.1:1 to about 1.9:1, about 1.2:1 to about 1.8:1, about 1.3:1 to about 1.7:1, or about 1.4:1 to about 1.6:1. In another implementation, the weight ratio of the silica to the base may be from about 0.1:5, about 0.2:5, about 0.3:5, about 0.5:5, about 1:5, about 1.5:5, or greater. In a preferred implementation, the weight ratio of the silica to the base may be from about 1.3:1 to about 1.7:1, about 1.3:1 to about 1.6:1, about 1.3:1 to about 1.5:1, or about 1.4:1.

The CSS particles formed from contacting the silica particles with the base having the first metal ion, or the CSS particles including the first metal silicate, may have a relatively high charge density and/or ion exchange capacity. In at least one implementation, the CSS particles including the first metal silicate along the surface thereof may have a surface charge density of from about 0.5 meg/g of silica to about 4.5 meg/g of silica. For example, the CSS particles including the first metal silicate along the surface thereof may have a surface charge density of from about 0.5 meg/g of silica, about 1.0 meg/g of silica, about 1.5 meg/g of silica, or about 2.0 meg/g of silica to about 3.0 meg/g of silica, about 3.5 meg/g of silica, about 4.0 meg/g of silica, or about 4.5 meg/g of silica. In another example, the CSS particles including the first metal silicate along the surface thereof may have a surface charge density of from about 0.5 meg/g of silica to about 4.5 meg/g of silica, about 1.0 meg/g of silica to about 4.0 meg/g of silica, about 1.5 meg/g of silica to about 3.5 meg/g of silica, about 2.0 meg/g of silica to about 3.0 meg/g of silica, or from about 2.45 meg/g silica to about 2.55 meg/g silica.

The CSS particles formed from contacting the silica particles with the base having the first metal ion, or the CSS particles including the first metal silicate, may have a charge or ion exchange capacity of from about 0.05 C/cm² surface area to about 0.1 C/cm² surface area. For example, the CSS particles including the first metal silicate may have a charge or ion exchange capacity of from about 0.06 C/cm² surface area to about 0.1 C/cm² surface area, about 0.085 C/cm² surface area to about 0.095 C/cm² surface area, or about 0.089 C/cm² surface area.

As discussed above, the method may also include reacting or otherwise contacting the CSS particles having the first metal silicate along the surface thereof with a metal salt including the second metal ion to provide the surface of the CSS particles with a silicate of the second metal ion, or the second metal silicate. It should be appreciated that the second metal ion of the metal salt may displace or ion exchange with the monovalent metal ion of the first metal silicate disposed along the surface of the CSS particles. The second metal silicate formed along the surface of the silica core may be represented by formula (2),

$$M^2SiO_3 \cdot xH_2O \quad (2)$$

where $M^2$ is a divalent metal ion, and x is an integer from 0 to 10. In a preferred embodiment, the second metal silicate formed along the surface of the silica core may be represented by formula (3),

$$Zn^2SiO_3 \cdot xH_2O \quad (3)$$

where x is an integer from 0 to 10.

The metal salt may include any second metal ion capable of or configured to displace the monovalent metal ion of the first metal silicate. The second metal ion may be a group 2 or alkaline earth metal ion, a transition metal ion, a group 13 metal ion, a group 14 metal ion, and mixtures thereof. The second metal ion may be or include a divalent metal ion, a trivalent metal ion, a tetravalent metal ion, and mixtures thereof. In a preferred implementation, the second metal ion is a divalent metal ion. Illustrative second metal ions may be or include, but are not limited to, $Ca^{2+}$, $Mg^{2+}$, $Zn^{2+}$, $Sn^{2+}$, $Sr^{2+}$, $Al^3$, $Zr^{4+}$, $Ti^{4+}$, $Fe^{3+}$, $Fe^{2+}$, $Mo^{2+}$, $Co^{2+}$, $Ni^{2+}$, $Mn^{2+}$, $Cu^{2+}$, $Pd^{2+}$, $Mo^{2+}$, $Ru^{2+}$, and mixtures thereof.

Illustrative metal salts may be or include, but are not limited to, metal acetates, metal borates, metal butyrates, metal carbonates, metal halides, metal citrates, metal formates, metal gluconates, metal glycerates, metal glycolates, metal lactates, metal oxides, metal phosphates, metal picolinates, metal proprionates, metal salicylates, metal silicates, metal stearates, metal tartrates, metal undecylenates, and the like, and mixtures or combinations thereof. In a preferred embodiment the metal salt is a metal halide, such as a metal chloride. Illustrative metal chlorides may be or include, but are not limited to $ZnCl_2$, $SnCl_2$, $SrCl_2$, $AlCl_3$, $FeCl_3$, $TiCl_4$, $ZrCl_4$, and the like, and combinations thereof. In a preferred implementation, the metal salt is a zinc salt. Illustrative zinc salts may be or include, but are not limited to, zinc acetate, zinc borate, zinc butyrate, zinc carbonate, zinc chloride, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate, and the like, and mixtures or combinations thereof. In a preferred implementation, the metal salt is zinc chloride ($ZnCl_2$).

The metal salt may be provided as a solid or an aqueous solution. For example, the metal salt may be provided as crystalline solids or powders. In another example, the metal salt may be dissolved or dispersed in an aqueous (e.g., water) or non-aqueous solution.

In at least one implementation, the method may include mixing or otherwise contacting the metal salt with a humectant prior to contacting the metal salt with the CSS particles having the first metal silicates. For example, the method may include preparing an aqueous solution of the metal salt and the humectant, and subsequently contacting the CSS particles having the first metal silicate with the aqueous solution of the metal salt and the humectant, or the metal salt/humectant solution. Illustrative humectants may be or include, but are not limited to, ethanol, polyhydric alcohol, such as glycerin, glycol, inositol, maltitol, mannitol, sorbitol, xylitol, propylene glycol, polypropylene glycol (PPG), polyethylene glycol (PEG), and the like, and mixtures or combinations thereof. Illustrative humectants may also be or include, but are not limited to, saccharide, such as fructose, glucose, sucrose, and the like, and combinations or mixtures thereof.

A weight ratio of the humectant to the base may vary widely. In at least one implementation, the weight ratio of the humectant to the base may be from greater than or equal to 0.5:1 to less than or equal to 10:1. For example, the weight ratio of the humectant to the base may be from about 0.5:1, about 1:1, about 1.5:1, about 2:1, about 2.5:1, about 3:1, about 3.5:1, about 4:1, about 4.5:1, about 5:1, about 5.5:1, about 6.0:1, about 6.2:1, or about 6.4:1 to about 6.6:1, about 6.8:1, about 7:1, about 7.5:1, about 8:1, about 8.5:1, about 9:1, about 9.5:1, or about 10:1. In another implementation, the weight ratio of the humectant to the base may be from greater than or equal to 4.5:1 to less than or equal to 8.5:1. For example, the weight ratio of the humectant to the base may be from about 4.5:1, about 5:1, about 5.5:1, about 6.0:1, about 6.2:1, or about 6.4:1 to about 6.6:1, about 6.8:1, about 7:1, about 7.5:1, about 8:1, or about 8.5:1. In another example, the weight ratio of the humectant to the base may be from about 4.5:1 to about 8.5:1, about 5:1 to about 8:1, about 5.5:1 to about 7.5:1, about 6.0:1 to about 7:1, about 6.2:1 to about 6.8:1, or about 6.4:1 to about 6.6:1. In a preferred implementation, the weight ratio of the humectant to the base may be from about 6.2:1 to about 6.8:1, about 6.3:1 to about 6.5:1, or about 6.4:1.

A weight ratio of the humectant to the metal salt may vary widely. In at least one implementation, the weight ratio of the humectant to the metal salt may be greater than or equal to 2:1 and less than or equal to 15:1. For example, the weight ratio of the humectant to the metal salt may be from about 2:1, about 2.5:1, about 3:1, about 3.5:1, about 4:1, about 4.5:1, about 5:1, about 5.5:1, about 6:1, about 6.5:1, about 7:1, or about 7.5:1 to about 8:1, about 8.5:1, about 9:1, about 9.5:1, about 10:1, about 10.5:1, about 11:1, about 11.5:1, about 12:1, about 12.5:1, about 13:1, about 13.5:1, about 14:1, about 14.5:1, or about 15:1. In another implementation, the weight ratio of the humectant to the metal salt may be greater than or equal to 10:1 and less than or equal to 13:1. For example, the weight ratio of the humectant to the metal salt may be from about 10:1, about 10.5:1, about 11:1, about 11.2:1, or about 11.4:1 to about 11.6:1, about 11.8:1, about 12:1, about 12.5:1, or about 13:1. In another example, the weight ratio of the humectant to the metal salt may be from about 10:1 to about 13:1, about 10.5:1 to about 12.5:1, about 11:1 to about 12:1, about 11.2:1 to about 11.8:1, or about 11.4:1 to about 11.6:1. In a preferred implementation, the weight ratio of the humectant to the metal salt may be from about 11.4:1 to about 11.6:1, more preferably about 11.5:1.

The metal salt/humectant solution may have an acidic pH. For example, the metal salt/humectant solution may have a pH of from greater than or equal to 1 to less than 7. In another example, the pH of the metal salt/humectant solution may be from about 1, about 2, about 3, or about 4 to about 5, about 6, or less than 7. In yet another example, the pH of the metal salt/humectant solution may be from about 1 to about 7, about 2 to about 6, or about 3 to about 5. In a preferred implementation, the metal salt/humectant solution may have a pH of from about 3.5 to about 4.5, more preferably about 4.

As further described herein, the dropwise, stepwise, or otherwise incremental addition of the metal salt to the CSS particles having the first metal silicate may result in competing reactions that produces metal oxides (e.g., ZnO) and reduces the yield of the CSS particles having the second metal silicate. As such, contacting the CSS particles having the first metal silicate with the metal salt may include dropwise, stepwise, or otherwise incremental addition of the CSS particles having the first metal silicate to the metal salt. For example, contacting the CSS particles having the first metal silicate with the metal salt may include incrementally adding the CSS particles having the first metal silicate to an aqueous solution of the metal salt (e.g., $ZnCl_2$ solution). The aqueous solution of the metal salt may be maintained in a first vessel or container and the CSS particles having the first metal silicate may be maintained in a second vessel or container, and the CSS particles in the second container may be slowly or incrementally added to the first container such that only a relatively small amount of the CSS particles are available to react with the metal salt in the aqueous solution. In another example, contacting the CSS particles having the first metal silicate with the metal salt may include incrementally adding the CSS particles having the first metal silicate to a metal salt/humectant solution (e.g., aqueous solution of the metal salt and the humectant). In a preferred embodiment, the CSS particles having the first metal silicate may be incrementally added to an aqueous solution of $ZnCl_2$ and sorbitol, where the aqueous solution may have a pH of from about 3 to about 5, about 3.5 to about 4.5, or about 4.

The CSS particles having the first metal silicate may be incremental added to the metal salt over a predetermined period of time. For example, the CSS particles having the first metal silicate may be incremental added to the metal salt over a period of at least 1 min, at least 2 min, at least 5 min, at least 10 min, at least 20 min, at least 30 min, at least 1 hour, at least 2 hours, at least 3 hours, at least 4 hours, at least 5 hours, at least 10 hours, at least 15 hours, at least 20 hours, at least 24 hours, at least 2 days, at least 4 days, or more.

The CSS particles formed from contacting the CSS particles having the first metal silicate with the metal salt, or the CSS particles including the second metal silicate, may include a silica core where the surface of the silica core is etched with the second metal silicate. It should be appreciated that the second metal silicate may be a silicate of the group 2 or alkaline earth metal ion, a transition metal ion, a group 13 metal ion, a group 14 metal ion, and mixtures thereof.

In at least one implementation, contacting the CSS particles including the first metal silicate with the metal salt may form or provide the surface of the CSS particles with the first metal silicates and the second metal silicates. For example, the second metal ion of the metal salt may substitute or ion exchange entirely or with only a portion of the first metal ions of the first metal silicates (i.e., incomplete ion exchange). In at least one implementation, the CSS particles may have a ratio of the first metal silicates to the second metal silicates of from about 1:1 to about 1:4. For example, the CSS particles may have a ratio of the first metal silicates to the second metal silicates of from about 1:1, about 1:1.5, or about 1:2 to about 1:3, about 1:3.5, or about 1:4. In another example, the CSS particles may have a ratio of the first metal silicates to the second metal silicates of from about 1:1 to about 1:4, about 1:1.5 to about 1:3.5, or about 1:2 to about 1:3. In another implementation, the CSS particles may have a ratio of the first metal silicates to the second metal silicates of from about 1:1 to about 1:10. For example, the CSS particles may have a ratio of the first metal silicates to the second metal silicates of from about 1:1, about 1:1.5, about 1:2, about 1:2.5, about 1:3, about 1:3.5, about 1:4, about 1:4.5, or about 1:5 to about 1:6, about 1:6.5, about 1:7, about 1:7.5, about 1:8, about 1:8.5, about 1:9, about 1:9.5, or about 1:10. In another example, the CSS particles may have a ratio of the first metal silicates to the second metal silicates of from about 1:1 to about 1:10, about 1:1.5 to about 1:9.5, about 1:2 to about 1:9, about 1:2.5 to about 1:8.5, about 1:3 to about 1:8, about 1:3.5 to about 1:7.5, about 1:4 to about 1:7, about 1:4.5 to about 1:6.5, or about 1:5 to about 1:6.

In another implementation, contacting the CSS particles including the first metal silicate with the metal salt may form or provide the surface of the CSS particles with the second metal silicates. For example, all or substantially all of the first metal ion of the first metal silicate may ion exchange with the second metal ion of the metal salt. For example, at least 85%, at least 90%, at least 95%, at least 98%, or at least 99% of the first metal ion of the first metal silicate may ion exchange with the second metal ion of the metal salt.

In yet another implementation, the second metal silicate may be present in an amount of at least 30 weight %, at least 40 weight %, at least 50 weight %, at least 60 weight %, at least 70 weight %, at least 80 weight %, at least 90 weight %, or at least 95 weight % of the total metal silicate (i.e., first metal silicate and second metal silicate) of the CSS particles.

The CSS particles including the second metal silicate may be capable of being disposed in a dentin tubule of a human. For example, at least a portion of the CSS particles including the second metal silicate may be sized to be disposed into the dentin tubule of a human or non-human subject.

The CSS particles including the second metal silicate may include from greater than 0 weight % to less than or equal to 40 weight % of the second metal ion (e.g., Zn), based on a total weight of the CSS particles. For example, the amount or concentration of the second metal ion in the CSS particles may be from greater than 0 weight %, about 5 weight %, about 10 weight %, about 15 weight %, or about 20 weight % to about 25 weight %, about 30 weight %, or about 40 weight %, based on a total weight of the CSS particles. In another example, the amount or concentration of the second metal ion in the CSS particles may be from about 0 weight % to about 40 weight %, about 5 weight % to about 35 weight %, about 10 weight % to about 30 weight %, about 15 weight % to about 25 weight %, or about 20 weight % to about 25 weight %, based on a total weight of the CSS particles.

In at least one implementation, the amount of the second metal ion adsorbed to the surface of the CSS particles may be from greater than 0% to less than or equal to about 40% of a maximum ion-exchange capacity of the CSS particle for divalent ions. For example, the amount of the second metal ion adsorbed to the surface of the CSS particles may be from about 0%, about 5%, about 10%, about 15%, or about 20% to about 25%, about 30%, about 35%, or about 40%, of a maximum ion-exchange capacity of the CSS particle for divalent ions. In another example, the amount of the second metal ion adsorbed to the surface of the CSS particles may be from greater than 0% to about 40%, about 5% to about 35%, about 10% to about 30%, about 15% to about 25%, or about 20% to about 25% of a maximum ion-exchange capacity of the CSS particle for divalent ions.

Compositions

The present disclosure may provide oral care compositions including the CSS particles disclosed herein. For example, the oral care compositions may include the core shell silica (CSS) particles as defined above and a carrier or orally acceptable vehicle. As used herein, "orally acceptable vehicle" may refer to a suitable vehicle, ingredient, or combination of ingredients, which can be used to form and/or apply the oral care composition to the surfaces of the oral cavity in a safe and effective manner. It should be appreciated that the orally acceptable vehicle may include materials such as, but not limited to, one or more antibacterial agents, anticalculus agents, buffers, additional abrasives, sources of peroxide (e.g., hydrogen peroxide), alkali metal bicarbonate salts, thickening materials, humectants, water, surfactants, titanium dioxide, cooling agents, coloring agents, and the like, and combinations thereof. For oral care compositions, the second metal ion is preferably zinc. It should be appreciated that zinc core shell silica (ZnCSS) may provide anti-bacterial and anti-malodor properties to the oral care compositions, and an improved taste profile over free zinc salts such as $ZnCl_2$.

In at least one implementation, the compositions (e.g., oral care compositions) may include from about 0.1 weight % to about 20 weight % of the CSS particles, based on a total weight of the composition. For example, the CSS particles may be present in an amount of about 0.1 weight %, about 2 weight %, about 4 weight %, about 6 weight %, about 8 weight %, or about 9 weight % to about 11 weight %, about 12 weight %, about 14 weight %, about 16 weight %, about 18 weight %, or about 20 weight %, based on a total weight of the composition. In another example, the CSS particles may be present in an amount of about 0.1 weight % to about 20 weight %, about 2 weight % to about 18 weight %, about 4 weight % to about 16 weight %, about 6 weight % to about 14 weight %, about 8 weight % to about 12 weight %, or about 9 weight % to about 11 weight %, based on a total weight of the composition.

The composition incorporating the CSS particles may be a solid, a paste, a gel, or a liquid. Illustrative compositions may be or include, but are not limited to, a dentifrice (e.g., a toothpaste, dental gel, dental cream, or tooth powder), a mouthwash, mouth rinse, or mouth spray, an oral slurry or liquid dentifrice, a gum or other confectionary, a lozenge, dental floss or dental tape, a prophylaxis paste or powder, a mono- or multi-layer oral film or gel strip (e.g., tooth strips or breath strips), functional film or gel flakes or functional micro- or nano-particles, a film-forming composition including pre-gel(s) or pre-polymer(s) (e.g., film-forming dentifrices), dental paints, a tooth hardener, or a coating on an oral device (e.g., orthodontic, appliance or implant).

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

Core shell silica (CSS) particles having a first metal silicate were prepared. Particularly, silica (i.e., ZEODENT® 105) was dispersed in hot water with a silica/water weight ratio of from about 0.3 to about 1.5. The temperature of this solution was from about 40° C. to about 70° C. Then, a base (i.e., 45% KOH aqueous solution) was added into the silica slurry at a silica/base weight ratio of from about 0.2 to about 5. The reaction time was varied from 2 min to 20 min. The base etched surfaces of the silica to provide a silicate rich surface, thereby providing CSS particles having the first metal silicate along surfaces thereof. In this example, the CSS particles prepared had potassium silicates along the surface thereof, thereby providing potassium core shell silica (KCSS) particles.

Example 2

The KCSS particles prepared in Example 1 were utilized for the preparation of CSS particles having the second metal silicates. Particularly, zinc core shell silica (ZnCSS) particles were prepared according to a control or conventional method.

According to the control method, a metal salt, here a zinc chloride ($ZnCl_2$) powder, was added to the KCSS particles prepared in Example 1. Particularly, the $ZnCl_2$ powder was added to an aqueous dispersion of the KCSS prepared in Example 1, without heating. The mixing time was varied from 3 min to 20 min. It should be appreciated that the aqueous dispersion had a basic pH (about 11) due to the high concentration of KOH. Upon addition of the $ZnCl_2$, however, the solution solidified, thereby preventing further mixing.

Without being bound by theory, it is believed that the relatively high concentration of the base, or KOH, in the mixture resulted in the formation or precipitation of large amounts of metal hydroxides and/or metal oxides, such as zinc hydroxide ($Zn(OH)_2$) and/or zinc oxide (ZnO), respectively, via competing reactions. It is further believed that the zinc hydroxide and/or the zinc oxide that precipitated strongly interacted with one another to form networking or interacting structures that thickened or solidified the mixture. The solidification of the mixture prevented further reaction between the $ZnCl_2$ and the KCSS; and thus, prevented the formation or a high yield of the ZnCSS particles.

Example 3

The KCSS particles prepared in Example 1 were utilized for the preparation of CSS particles having the second metal silicates. Particularly, zinc core shell silica (ZnCSS) particles were prepared according to a test or reverse addition method.

In the reverse addition method, the KCSS was added to a metal salt/humectant aqueous solution. Particularly, a humectant (i.e., sorbitol) in amounts varying from 15-35 g and $ZnCl_2$ in an amount of about 2 g was combined with water varying from 5 to 20 g to prepare the metal salt/humectant aqueous solution, and the KCSS particles, about 15-30 g, prepared from Example 1 were added into the metal salt/humectant aqueous solution. It was surprisingly and unexpectedly discovered that the addition of the KCSS particles of Example 1 to the metal salt/humectant aqueous solution resulted in a uniform opaque mixture/solution having the ZnCSS particles dispersed therein. It should be appreciated that the metal salt/humectant aqueous solution had an acidic pH of about 4.

Without being bound by theory, it is believe that the low, acidic pH conditions prevented the formation of the metal hydroxides and/or the metal oxides. Particularly, the acidic pH prevented the competing reactions that formed the $Zn(OH)_2$ and/or the ZnO, thereby allowing the substantially complete ion exchange between the $ZnCl_2$ and the potassium (K) of the KCSS.

Example 4

ZnCSS particles were prepared according to a traditional or conventional method, as discussed and described in U.S. application Ser. No. 15/106,426, filed Dec. 18, 2014, and published as U.S. Pub. No. 2016/0338919. Particularly, 2826.3 g of water and 224.6 g of a 45% KOH aqueous solution was combined with one another in a reaction chamber under mechanical stirring, and subsequently heated to a temperature above 100° C. The silica particles (ZEODENT® 105) in an amount of 560.1 g was incrementally or slowly added to the heated aqueous solution, and the mixture was heated/reacted for at least 4 hours to prepare the NaCSS colloids. Then, 180.18 g of $ZnCl_2$ was dissolved in 1 of heated water (75° C.) to prepare a $ZnCl_2$ solution. The $ZnCl_2$ solution was then slowly added to the KCSS colloidal suspension under stirring and allowed to react for at least 1 hour at 85° C. After adding the $ZnCl_2$ solution to the KCSS colloidal suspension, the mixture was allowed to cool to room temperature and stirred overnight. The resulting mixture, including the ZnCSS particles, was filtered to collect the ZnCSS particles, which were subsequently washed.

Example 5

Analytical analysis was performed on raw silica particles (ZEODENT® 105), the ZnCSS particles prepared according to the methods Example 3, the reverse addition method, and Example 4, the conventional method. Particularly, Fourier transform infrared spectroscopy (FTIR) analysis was conducted on the raw silica (ZEODENT® 105) and the ZnCSS particles prepared according to Examples 3 and 4. The results of the FTIR are illustrated in FIG. 1.

With continued reference to FIG. 1, the peak at about 800 $cm^{-1}$ is associated with vibrations of the Si—O bond in silica, and the peak at about 960 $cm^{-1}$ is associated with the vibrations of the silicate group. As illustrated by the relatively high peak at 960 $cm^{-1}$ as compared to the raw silica particles (ZEODENT® 105), the ZnCSS particles prepared according to the reverse addition method of Example 3 exhibited a relatively greater amount of silicate groups than the ZnCSS prepared according to the conventional method of Example 4 and the raw silica particles. The results of the FTIR analysis demonstrated that the ZnCSS prepared by the reverse addition method of Example 3 exhibited a relatively greater amount of surface active silicate groups than the ZnCSS prepared by the conventional methods of Example 4.

Example 6

Analytical analysis was performed on the silica (ZEODENT® 105) and the ZnCSS particles prepared according to the methods of Example 3, the reverse addition method, and Example 4, the conventional method. Particularly, electron spectroscopy for chemical analysis (ESCA) analysis was conducted on the silica (ZEODENT® 105) and the ZnCSS particles prepared according to Examples 3 and 4. ESCA was used to determine the surface composition of the respective ZnCSS particles. The results of the ESCA are summarized in Table 1.

TABLE 1

Summary of ESCA Analysis

| Sample | Atomic Percentage | | | | | | Atomic Ratio | |
|---|---|---|---|---|---|---|---|---|
| | $O_{total}$ | Si | $O_{SiO3}$ | K | Zn | Cl | Si/O | $O_{SiO3}/(2Zn + K)$ |
| ZnCSS of Example 3 w/1.6% $ZnCl_2$ | 65.56 | 26.72 | 8.2 | 2.45 | 5.29 | 0 | 0.41 | 0.63 |
| ZnCSS of Example 3 w/2.0% $ZnCl_2$ | 66.54 | 25.92 | 5.46 | 1.05 | 6.50 | 0 | 0.39 | 0.39 |
| ZnCSS of Example 4 | 66.89 | 28.07 | 3.33 | 0.77 | 4.10 | 0.18 | 0.42 | 0.37 |
| Raw Silica ZEODENT ®105 | 69.30 | 30.30 | 0 | 0.41 | — | — | 0.44 | — |

As illustrated in Table 1, the amount oxygen in silicate ($O_{SiO3}$) and Zinc in the ZnCSS particles prepared according to the reverse addition method of Example 3 was relatively higher (8.2%) than the $O_{SiO3}$ of the ZnCSS particles prepared according to the conventional method of Example 4 (3.33%). The ESCA analysis demonstrated that the CSS prepared by the reverse addition method could provide CSS particles having as much as two times more surface silicate groups than CSS prepared according to the conventional method.

Example 7

Calcium CSS particles (CaCSS) were prepared according to the reverse addition method and the conventional method. The procedures for the conventional method and the reverse addition method were similar to those disclosed in Example 3 and Example 4, respectively, except the $ZnCl_2$ was replaced with $CaCl_2 \cdot 2H_2O$. ESCA analysis was conducted on the CaCSS prepared. The results of the ESCA are summarized in Table 2.

TABLE 2

Summary of ESCA Analysis

| Sample | Atomic Percentage | | | | | | Atomic Ratio | |
|---|---|---|---|---|---|---|---|---|
| | $O_{total}$ | Si | $O_{SiO3}$ | K | Ca | Cl | Si/O | $O_{SiO3}/(2Ca + K)$ |
| CaCSS Reverse Addition | 68.23 | 27.42 | 7.65 | 0.28 | 4.07 | 0 | 0.40 | 0.91 |
| CaCSS Conventional | 67.72 | 28.25 | 4.85 | 1.43 | 2.13 | 0.48 | 0.42 | 0.85 |

As illustrated in Table 2, the CaCSS prepared according to the reverse addition method exhibited about 1.5 times more surface silicate groups and 2 times more surface calcium. The results demonstrate that the reverse addition method is not limited to zinc chloride, but may also be applied to other metal salts.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A method of preparing core shell silica particles, comprising:
    contacting silica particles with a base comprising a first metal ion to produce core shell silica particles, each of the core shell silica particles comprising a silica core and a silicate of the first metal ion etched on a surface of the silica core; and
    contacting each of the core shell silica particles comprising the silicate of the first metal ion with an acidic aqueous solution comprising a metal salt having a second metal ion to produce core shell silica particles comprising the silica core and a silicate of the second metal ion on the surface of the silica core,
    wherein contacting each of the core shell silica particles with the acidic aqueous solution comprises incrementally adding the core shell silica particles to the acidic aqueous solution and wherein the acidic aqueous solution further comprises a humectant.

2. The method of claim 1, wherein the first metal ion is a monovalent ion, optionally a group 1 metal ion.

3. The method of claim 1, wherein the humectant is at least one of ethanol, polyhydric alcohol, such as glycerin, glycol, inositol, maltitol, mannitol, sorbitol, xylitol, propylene glycol, polypropylene glycol (PPG), and polyethylene glycol (PEG).

4. The method of claim 3, wherein the humectant is sorbitol.

5. The method of claim 1, wherein the silica particles comprise at least one of precipitated silica, fumed silica, and fused silica.

6. The method of claim 1, wherein the base comprises at least one of sodium hydroxide, potassium hydroxide, sodium carbonate, potassium carbonate, trisodium phosphate, disodium phosphate, potassium phosphate, dipotassium phosphate, tetrasodium pyrophosphate, and tetrapotassium pyrophosphate.

7. The method of claim 1, wherein the base comprises potassium hydroxide or sodium hydroxide.

8. The method of claim 1, wherein a weight ratio of the silica particles to the base is from about 0.1:1 to less than 4:1, 0.1:1 to less than 3:1, about 1.3:1 to about 1.5:1, or about 1.4:1.

9. The method of claim 1, wherein the second metal ion is a divalent metal ion, a trivalent metal ion, or a tetravalent metal ion.

10. The method of claim 1, wherein the metal salt is a zinc salt, and the second metal ion is $Zn^{2+}$.

11. The method of claim 1, wherein a weight ratio of the humectant to the base is from about 4.5:1 to about 8.5:1, about 6.2:1 to about 6.8:1, about 6.3:1 to about 6.5:1, or about 6.4:1.

12. The method of claim 1, wherein a weight ratio of the humectant to the metal salt is from about 10:1 to about 13:1, about 11.4:1 to about 11.6:1, or about 11.5:1.

13. The method of claim 1, wherein the acidic aqueous solution has a pH of less than 7, about 3.5 to about 4.5, or about 4.

\* \* \* \* \*